United States Patent
Bishop et al.

(10) Patent No.: US 8,226,956 B2
(45) Date of Patent: *Jul. 24, 2012

(54) **EXTRACT OF *R. MIEHEI***

(75) Inventors: Michael Bishop, Dallas, TX (US); Elysiann Bishop, Dallas, TX (US); Glen Gillis, Denton, TX (US)

(73) Assignee: Active Organics, Inc., Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/396,909

(22) Filed: Feb. 15, 2012

(65) Prior Publication Data

US 2012/0142599 A1    Jun. 7, 2012

Related U.S. Application Data

(60) Continuation of application No. 12/793,427, filed on Jun. 3, 2010, now Pat. No. 8,142,792, which is a division of application No. 11/329,146, filed on Jan. 11, 2006, now Pat. No. 7,776,339.

(51) Int. Cl.
    *A61K 36/09* (2006.01)
(52) U.S. Cl. .................................... 424/195.15
(58) Field of Classification Search .......... None
    See application file for complete search history.

(56) References Cited

U.S. PATENT DOCUMENTS

| | | | |
|---|---|---|---|
| 4,526,792 A | | 7/1985 | Granday et al. |
| 4,743,551 A | * | 5/1988 | Subramanian ................ 435/226 |
| 5,597,558 A | | 1/1997 | Aubert et al. |
| 5,607,980 A | | 3/1997 | McAtee et al. |
| 6,197,319 B1 | | 3/2001 | Wang et al. |
| 6,277,892 B1 | | 8/2001 | Deckner et al. |
| 6,303,752 B1 | | 10/2001 | Olsen et al. |
| 6,492,326 B1 | | 12/2002 | Robinson et al. |
| 6,509,171 B1 | | 1/2003 | Berka et al. |
| 6,569,437 B1 | | 5/2003 | Bishop et al. |
| 6,656,701 B2 | | 12/2003 | Bishop et al. |
| 6,846,812 B2 | | 1/2005 | Dalko et al. |
| 7,410,946 B2 | | 8/2008 | Rayner et al. |
| 7,776,339 B2 | | 8/2010 | Bishop et al. |
| 2010/0310598 A1 | | 12/2010 | Bishop et al. |

FOREIGN PATENT DOCUMENTS

| | | |
|---|---|---|
| EP | 1 514 537 A2 | 3/2005 |
| WO | 2007082001 A3 | 7/2007 |

OTHER PUBLICATIONS

International Search Report for PCT/US2007/000658 dated Nov. 1, 2007.
Written Opinion for PCT/US2007/000658 dated Sep. 12, 2007.
EPO Extended Search Report for 07716505.8 dated Apr. 27, 2010.

* cited by examiner

*Primary Examiner* — Melenie McCormick
*Assistant Examiner* — Randall Winston
(74) *Attorney, Agent, or Firm* — Christopher P. Demas

(57) ABSTRACT

Topical compositions comprising extracts of *Rhizomucor miehei* that are substantially devoid of acid-protease activity and their use in treating dermatologic conditions, including reducing the appearance of signs of skin aging.

12 Claims, No Drawings

EXTRACT OF R. MIEHEI

This application is a Continuation of U.S. patent application Ser. No. 12/793,427, filed Jun. 3, 2010, which is a Divisional of U.S. patent application Ser. No. 11/329,146, filed Jan. 11, 2006, now U.S. Pat. No. 7,776,339, the contents of each of which are incorporated by reference herein in their entirety.

FIELD OF INVENTION

The present invention is directed to novel topical compositions comprising extracts of *Rhizomucor miehei* that are substantially devoid of acid-protease activity and their use in treating dermatologic conditions, including reducing the appearance of signs of skin aging.

BACKGROUND OF THE INVENTION

In order for milk to coagulate and eventually form cheese, enzymes must be added to breakdown the proteins that keep milk a liquid. More particularly, when proteins are denatured or otherwise modified, milk loses its liquid structure and begins to coagulate. Rennets, milk-coagulating enzymes traditionally obtained from the abomasum (the fourth stomach of the calf) have long been used in cheese making. The main enzyme in calf rennet is chymosin.

Calf-rennet, however, is expensive and has increasingly been replaced with rennet derived from microorganisms. U.S. Pat. No. 4,526,792 discloses the use of *R. miehei* as microbial rennet in the production of cheese. (All documents cited are, in relevant, part, incorporated herein by reference.) *R. miehei* does not contain chymosin, but instead acid proteases, which are similar in function to chymosin.

Among the commercially-available *R. miehei* extracts, several possess some degree of enzymatic activity, principally from acid proteases. An extract substantially devoid of acid-protease activity can, however, be obtained by the removal of enzymatic activity by a number of well-known biochemical processes. The resulting non-enzymatic milieu is substantially devoid of enzymatic activity. A number of methods well-known to those skilled in the art to remove enzymatic activity are known and include affinity gel column chromatography and subsequent elution of the adsorbed microbial rennet. See, e.g., Kobayashi, et al., "Rapid isolation of microbial milk-clotting enzymes by N-acetyl-(or N-isobutyryl)-pepstatin-aminohexylagarose" *Anal. Biochem.*, 122: 308-312 (1982) (microbial rennet from *R. miehei* purified by use of affinity gel column using N-acetylpepstatin as affinity ligand). Enzymes can also be separated on affinity gel columns using Cibacron Blue F3GA ("CB"). See, e.g., Dean, et al., "Protein purification using immobilized triazine dyes," *J. Chromatogr.*, 165: 301-319 (1979) and Burgett, et al., "Cibacron Blue F3GA affinity chromatography", *Am. Lab.*, 9(5): 74, 78-83 (1977) (describing separation of enzymes on CB columns, including for example, kinases and nucleases). U.S. Pat. No. 4,743,551 describes the use of a blue dye affinity ligand and elution of the adsorbed rennet to produce a purified *R. miehei* rennet. A proteinaceous extract of *R. miehei* substantially devoid of acid-protease activity can also obtained by other techniques well-known to those of skill in the art, including thermal inactivation and molecular weight sieve.

There exists a delicate homeostatic balance between the rates of synthesis and degradation in the skin cells and underlying connective tissues including collagen and elastin, the principal structural proteins in mammalian skin. This balance allows the cells and tissues to regenerate as well as repair and replace damaged cells and tissues caused by environmental stressors. Thus, in the case of collagen, both endogenous and exogenous signals regulate the transcription of collagen mRNA and its subsequent translation into non-structural collagen subunits known as procollagen. More particularly, procollagen undergoes post-translational modification, including hydroxylation of proline and lysine residues to hydroxyproline and hydroxylysine. Procollagen is susceptible to degradation by collagenases, including matrix metalloproteinases. After being secreted through Golgi apparatus, procollagen is further processed into collagen via proteolytic removal of noncollagenous portions of the polypeptide (i.e., by proteases). The collagen molecules are then assembled into mature collagen fibrils which, in turn are cross-linked, and are more resistant to metalloproteases.

The visible signs of aging (e.g., fine lines and wrinkles) are correlated with a decrease in the level of collagen in the skin. This is can be attributed both to decreased synthesis as well as increased enzymatic degradation by collagenases, in particular Collagenase I also known as Matrix Metalloprotease 1 (MMP1). The degradative activity of MMP1 is regulated by the concentration of an endogenous protease inhibitor, Tissue Inhibitor of Matrix Metalloprotease-1 (TIMP1).

Prior art compositions have attempted to increase collagen synthesis in the skin by a number of molecular mechanisms. See, e.g., U.S. Pat. No. 6,846,812. KTTKS is a pentapeptide is derived from a fragment of the C-terminal portion of Collagen I. It has been studied in detail by Katayama et al., "A pentapeptide from type I procollagen promotes extracellular matrix production," *J. Biol. Chem.*, 268(14): 9941-9944 (1993).

Another approach to reducing the appearance of the signs of aging has been to enhance epidermal cell turnover by applying exfoliants. Two widely-used classes of exfoliants well-known to those of skill in the art are acid proteases (e.g., Cathepsin D-like), see, e.g., U.S. Pat. Nos. 6,656,701 and 6,569,437, and hydroxycarboxylic acids (e.g., alpha-hydroxy acids, such as glycolic acid).

In a poster presented at the February 2005 annual meeting of the American Academy of Dermatology in New Orleans, Leyden et al. described the use of a botanical extract from *R. miehei* that has Cathepsin-D like activity to enhance epidermal cell renewal (i.e., exfoliation) and thereby improve the appearance of environmentally damaged skin. Suprisingly, the proteinaceous extract of *R. miehei* of the present invention that is substantially devoid of acid protease activity, reduces the appearance of the signs of aging by a primary mode of action that is not based on exfoliation.

Thus, there remains a long-felt but as yet unmet need to increase Collagen I by upregulating the gene(s) that codes for the synthesis of Collagen I, and/or decrease levels of MMP1, either by upregulating the gene(s) that codes for TIMP1 or downregulating the gene(s) that codes for the expression of MMP1. These needs are met by the proteinaceous extract of the present invention. Surprisingly, the extract of *R. miehei* of the present invention that is substantially devoid of acid protease activity upregulates expression not only of the aforementioned genes, but also notably upregulates the expression of genes that code for fibronectin and vimentin (extracellular matrix glycoproteins involved in cell adhesion, differentiation, and migration) as well as procollagen-lysine 2-oxoglutarate 5-dioxygenase (an enzyme involved in the crosslinking of procollagen to form mature bundled collagen fibers).

SUMMARY OF THE INVENTION

The present invention is directed to novel topical compositions comprising extract of *Rhizomucor miehei* substantially devoid of acid-protease activity that upregulates expression of the gene(s) that code for Collagen I thereby helping to reduce the appearance of the signs of aging in a dermatologically-acceptable carrier.

DETAILED DESCRIPTION OF THE INVENTION

The topical composition of the present invention comprises extract of *Rhizomucor miehei* that is substantially devoid of acid protease activity in a dermatologically-acceptable carrier.

For purposes of the present application, "substantially devoid of acid protease activity" means a composition in which the combined acid protease(s) present have a combined acid protease specific activity of less than about 500 HUT units/mg. In a preferred embodiment, the combined acid protease specific activity is less than about 50 HUT units/mg. Still more preferably, the combined acid protease specific activity is less than about 10 HUT units/mg.

Combined acid protease activity is measured using the following variation on the method described in Food Chemicals CODEX, pp. 496-497 (Washington, D.C.: National Academy Press, 1981): Hemoglobin substrate is prepared by mixing 2 g bovine hemoglobin into 80 ml distilled water. The solution is then titrated to pH 2 by adding, for example, phosphoric acid and/or citric acid. Additional distilled water is added for a total volume of 100 ml. The solution is separated into four equal portions. Each portion is titrated to the desired pH with 50% sodium hydroxide or 50% hydrochloric acid. These final solutions are then heated at 30° C. for 20 minutes and are then filtered through glass wool. Trichloroacetic acid ("TCA" stock is prepared by dissolving TCA in distilled water for a final concentration of 5% TCA.

For each sample for which proteolytic activity is to be measured, prepare tubes labeled "B" and "T". In each tube place 4 ml of the hemoglobin solution and place at 37° C. such that the sample is prewarmed to 37° C. Into the "T" tube, add 100 µg enzyme solution, swirl gently and incubate at 37° C. for 20 minutes. Next add 10 ml TCA stock solution to each tube. Into the "B" tube add an equal amount of the enzyme as added to the "T" tube. (This is the control for background absorbance.) Centrifuge each tube and filter each sample through a syringe filter and place the filtered sample into a quartz cuvette for reading the absorbance at 280 nm. The actual absorbance is determined by subtracting the "T" sample's absorbance from the background. A standard curve can be generated by measuring known quantities of protease.

One HUT unit of proteolytic activity, is defined as that amount of enzyme that produces, in one minute under the specified conditions of the assay, a hydrolysate whose absorbance at 280 nm is the same as that of a solution containing 1.10 µg per ml of tyrosine in 0.006 N hydrochloric acid. HUT units per gram are determined by the following formula:

$$\text{HUT/g} = (\text{absorbance at 280 nm} \times V)/(0.0084 \times T \times W)$$

where V is the final volume of the test solution,
T is the reaction time in minutes, and
W is the dry weight of the original enzyme sample used in the assay Protein concentration is determined by a method known in the art, such as, for example, the Bradford Assay which is described in Ausubel et al., (Eds.); *Current Protocols in Molecular Biology* (John Wiley & Sons, Inc., New York, 1994).

*Rhizomucor miehei*

*R. miehei* is an article of commerce available from a number of sources including Valley Research Inc. (South Bend, Ind.) and Novozymes (Bagsvaerd, Denmark).

*R. miehei* substantially devoid of acid protease activity is obtained by molecular weight sieve, thermal inactivation and pepstatin-affinity gel chromatography.

In the present invention, *R. miehei* is present at a concentration less than about 500 HUT units/mg. In a preferred embodiment, the combined acid protease specific activity is less than about 50 HUT units/mg. Still more preferably, the combined acid protease specific activity is less than about 10 HUT units/mg.

Dermatologically-Acceptable Carrier

The present invention further comprises a dermatologically-acceptable carrier, one that is suitable for topical application to the keratinous tissue and is compatible with the dermatocosmetic active ingredients described below. The carrier can be in a wide variety of forms, including, but not limited to, oil-in-water emulsions, water-in-oil emulsions, water-in-silicone emulsions, silicone-in-water emulsions, water-in-oil-in-water, and oil-in-water-in-oil emulsions, and oil-in-water-in-silicone emulsions. Suitable surfactants include anionic, cationic, amphoteric, zwitterionic and non-ionic, including those listed in U.S. Pat. No. 6,197,319.

The International Cosmetic Ingredient Dictionary and Handbook (10$^{th}$ Edition, 2004), published by the Cosmetic, Toiletries & Fragrance Association, describes a wide variety of non-limiting cosmetic and dermatopharmaceutical ingredients commonly used in the skin care industry, which are suitable for use in combination with the *R. miehei* extract of the present invention. Examples of these ingredients include: antioxidants, anti-inflammatory agents, anti-acne agents, antimicrobial agents, astringents, humectants, moisturizers, pH adjusters, skin bleaching/lightening agents, skin soothing/healing agents and agents that help decrease the appearance of signs of aging.

Non-limiting examples of anti-acne ingredients suitable for use in compositions of the present invention include: resorcinol, sulfur, salicylic acid, benzoyl peroxide, erythromycin, and zinc. Further examples of suitable anti-acne actives are described in U.S. Pat. No. 5,607,980.

Non-limiting examples of skin bleaching and lightening agents which may be topically delivered in the present invention include: hydroquinone, kojic acid, glabradin, ascorbic acid, magnesium ascorbyl phosphate and ascorbyl glucosamine.

Non-limiting examples of antioxidants/radical scavengers suitable for use in compositions of the present invention include: ascorbic acid (vitamin C) and its salts, ascorbyl esters of fatty acids, ascorbic acid derivatives (e.g., magnesium ascorbyl phosphate, sodium ascorbyl phosphate, ascorbyl sorbate); tocopherol (vitamin E) and its esters, including tocopherol sorbate, tocopherol acetate; butylated hydroxybenzoic acids and their salts; 6-hydroxy-2,5,7,8-tetramethyl-chroman-2-carboxylic acid; gallic acid and its alkyl esters, especially propyl gallate; uric acid and its salts and alkyl esters; sorbic acid and its salts; lipoic acid; amines (e.g., N,N-diethylhydroxylamine, amino-guanidine); sulfhydryl compounds (e.g., glutathione); coenzyme Q10 and its analogues, including without limitation, idebenone; dihydroxyfumaric acid and its salts; lycine pidolate; arginine pilolate; nordihydroguaiaretic acid; bioflavonoids; curcumin; lysine; 1-methionine; proline; superoxide dismutase; silymarin; tea extracts; *Vitis vinifera* (grape) skin/seed extracts; melanin; and *Rosmarinus officinalis* (rosemary) extracts.

Non-limiting examples of skin soothing and/or healing agents suitable for use in the present invention include: allantoin, aloe vera and its derivatives, betulinic acid, bisabolol, dipotassium glycyrrhizinate, oleonolic acid, panthenol and derivatives, pantothenic acid and its derivatives, and ursolic acid.

Non-limiting examples of agents that help decrease the appearance of signs of aging, include muccopolysaccharides (including hyaluronic acid), aldosamines (including n-acetyl glucosamines) and biologically-active short-chain peptides (e.g., tri-, tetra-, penta-, and hexapeptides, and mixtures thereof).

In a preferred embodiment of the present invention, one or more of the cosmetic ingredients are botanically-derived (e.g. extracts).

Preferred botanically-derived anti-bacterial agents include, but are not limited to, extract of *Laurus nobilis* (bay laurel), extract of *Larrea divaricata* (chapparal), extract of *Rosa canina* (rose hips) and extract of *Scutellaria galericulata* (skullcap).

Preferred botanically-derived anti-fungal agents include, but are not limited to, extract of *Laurus nobilis* (bay laurel), extract of *Commiphora myrrha* (myrrh) and extract of *Melaleuca alternifolia* (tea tree oil).

Preferred botanically-derived anti-inflammatory agents include, but are not limited to, extract of *Iris versicolor* (blue flag), extract of *Calendula officinalis* (calendula), extract of *Chamomilla recrutita* (chamomile), extract of *Tussilago farfara* (coltsfoot), extract of *Symphytum officinale* (comfrey) leaves, extract of *Tanacetum parthenium* (feverfew), extract of *Panax ginseng* (ginseng), extract of *Gynostemma pentaphyllum* (southern ginseng), extract of *Aesculus hippocastanum* (horse chestnut), extract of *Camellia oleifera* (Japanese green tea), extract of *Tilia cordata* (linden tree), extract of *Althea officinalis* (marsh mallow), extract of *Viola tricolor* (pansy), extract of *Mentha pulegium* (pennyroyal), extract of *Vinca minor* (periwinkle), extract of *Chaenomeles japonica* (quince) seed, extract of *Anthemis nobilis* (roman chamomile), extract of *Valeriana officinalis* (valerian) and extract of *Viola odorata* (violet).

Preferred botanically-derived agents that help decrease the appearance of signs of aging include those that stimulate production of collagen. Non-limiting examples of these ingredients include asiatic acid, maddecassic acid and asiaticoside.

Preferred botanically-derived antioxidants include, but are not limited to, extracts of *Camellia oleifera* (Japanese green tea), extracts of *Vitis vinifera* (grape) seed, extracts of *Punica granatum* (pomegranate), extracts of *Citrus grandis* (grapefruit), bioflavonoids, extracts of *Panax ginseng* (ginseng), extracts of *Gynostemma pentaphyllum* (southern ginseng), resveratrol, anthrocyanidines, monoterpenoids, diterpenoids and triterpenoids, Preferred botanically-derived astringent agents include, but are not limited to, extract of *Citrus medica limonum* (lemon), extract of *Citrus aurantifolia* (lime), extract of *Artium lappa* (burdock), extract of *Nasturtium officinale* (watercress), extract of *Hedera helix* (ivy), extract of *Hamamelis virginiana* (witch hazel), extract of *Myrica cerifera* (bayberry) rootbark, extract of *Quercus alba* (oak gall), extract of *Echinacea purpurea* (coneflower), extract of *Echinacea augustifolia* (native coneflower), extract of *Eugenia caryophyllus* (clove oil), extract of *Capsicum annum* (cayenne pepper), extract of *Mentha piperita* (peppermint oil), and extract of *Melaleuca altemifolia* (tea tree oil).

Preferred botanically-derived moisturizing agents include, but are not limited to, pectin, disaccharides, oligosaccharides, and polysaccharides extracted from *Aloe barbedensis*, algae, seaweed and sea grass.

Preferred botanically-derived skin bleaching/lightening agents include, but are not limited to, arbutin and glabradin.

The above-listed botanical extracts are commercially-available from Active Organics LP (Lewisville, Tex.).

Sunscreen actives may also be used in combination with the *R. miehei* extract of the present invention. These include the sunscreens currently listed by the US Food and Drug Administration in the Sunscreen Drug Products for Over-The-Counter Human Use Final Monograph published in 64 Federal Register pp. 27666-27693 (May 21, 1999). Other sunscreen active ingredients are accepted for use in countries outside the US and are also considered to be within the scope of the present invention.

Dermatopharmaceutical ingredients that can be used in combination with the *R. miehei* extract of the present invention are disclosed in U.S. Pat. No. 6,277,892, in Kerdel, et al., *Dermatologic Therapeutics* (2005), and in Hardman et al., *Goodman & Gilman's: The Pharmacological Basis of Therapeutics* (10th Edition, 2001). Further examples of cosmetic and/or dermatopharmaceutical ingredients which are suitable for use in the delivery system of the present invention are disclosed in U.S. Pat. Nos. 6,492,326.

The following examples are further illustrative of the present invention. The components and specific ingredients are presented as being typical, and various modifications can be derived in view of the foregoing disclosure within the scope of the invention. In these examples, the proteinaceous extract of *R. miehei* that is substantially devoid of acid-protease activity is referred to by its tradename Actipeptide™ M from Active Organics, LP (Lewisville, Tex.). All percentages, ratios and proportions herein are by weight, unless otherwise specified. All temperatures are in degrees Celsius unless otherwise specified.

FORMULATION EXAMPLES

Toner

| | |
|---|---|
| Deionized Water | 93.190% |
| Methyl Gluceth-20 | 1.000% |
| Potassium Sorbate | 0.100% |
| Sodium Benzoate | 0.100% |
| Phenoxyethanol | 0.600% |
| Citric acid | 0.010% |
| Mucor Miehei Extract, Butylene Glycol, and N-Acetylglucosamine (Actipeptide ™ M, Active Organics) | 5.000% |

Add ingredients sequentially in order listed. Mix until clear. End processing.

Face Cream

| Part A | |
|---|---|
| Deionized Water | 62.600% |
| Magnesium Aluminum Silicate | 0.400% |
| Xanthan Gum | 0.150% |
| Acrylates/$C_{10-30}$ Alkyl Acrylate Crosspolymer | 0.750% |

-continued

| Part B | |
|---|---|
| Butylene Glycol | 4.000% |
| Disodium EDTA | 0.050% |
| Part C | |
| Hydrogenated Lecithin | 0.500% |
| Caprylic/Capric Triglyceride | 8.000% |
| Simmondsia Chinensis (Jojoba) Seed Oil | 5.000% |
| Octyl Palmitate | 4.000% |
| Cetearyl Alcohol | 2.000% |
| PEG-8 Stearate | 1.000% |
| PEG-100 Stearate | 0.800% |
| Part D | |
| Triethanolamine 99% | 0.100% |
| Part E | |
| Aloe Barbadensis Leaf Juice (Activera ® 10x, Active Organics) | 5.000% |
| Phenoxyethanol | 0.500% |
| Potassium Sorbate | 0.100% |
| Methylisothiazolinone | 0.050% |
| Mucor Miehei Extract, Butylene Glycol, and N-Acetylglucosamine (Actipeptide ™ M, Active Organics) | 5.000% |

Sprinkle Magnesium Aluminum Silicate, Xanthan Gum, Acrylates/$C_{10-30}$ Alkyl Acrylate Crosspolymer into vortex of water. Mix and heat to 80° C. Add Part B to Part A, mix and hold the temperature at 80° C. In a separate vessel, mix Part C and heat to 75° C., mix until clear. Add Part C to Parts A and B, mix for 10 minutes. Add Part D to Parts ABC. Mix for 15 minutes. Switch to sweep mixing. Cool batch to 45° C. In a separate container, add ingredients in Part E. Mix until uniform. At 45° C., add Part E, to Parts ABCD. Mix and cool to 25° C. End processing.

Eye Cream

| Part A | |
|---|---|
| Deionized Water | 57.650% |
| Acrylates/C10-30 Alkyl Acrylate Crosspolymer | 0.300% |
| Panthenol | 0.100% |
| Potassium Sorbate | 0.100% |
| Disodium EDTA | 0.100% |
| Allantoin | 0.100% |
| Part B | |
| Caprylic/Capric Triglyceride | 2.000% |
| Dimethicone | 3.000% |
| Butyrospermum Parkii (Shea Butter) | 2.000% |
| Carthamus Tinctorius (Safflower) Seed Oil | 2.000% |
| Cetearyl Alcohol | 1.500% |
| Dimethiconol | 1.300% |
| Steareth-2 | 1.000% |
| Steareth-21 | 0.500% |
| Cyclomethicone | 5.000% |
| Part C | |
| Triethanolamine | 0.250% |
| Part D | |
| Carbomer 940 2% Solution | 10.000% |
| Part E | |
| Mucor Miehei Extract, Butylene Glydol, and N-Acetylglucosamine (Actipeptide ™ M, Active Organics) | 5.000% |

-continued

| Part F | |
|---|---|
| Sodium Hyaluronate (Actimoist ® Bio 2, Active Organics) | 2.000% |
| Phenonip | 1.000% |
| Aloe Barbadensis Leaf Juice (Activera ® 10X, Active Organics) | 5.000% |
| Tocopherol | 0.100% |

Sprinkle Acrylates/$C_{10-30}$ Alkyl Acrylate Crosspolymer into vortex of water. Mix and heat to 75° C. Mix and heat Part B to 70° C. Add Part B to Part A, mix for 10 minutes. Add Part C. Mix for 10 minutes. Add Part D. Mix and cool to 45° C. At 45° C., add Parts E and F. Mix and cool to 25° C. End processing.

Lipstick

| Part A | |
|---|---|
| Ricinus Communis (Castor) Seed Oil | 24.37% |
| Octyl Palmitate | 33.33% |
| Petrolatum | 10.84% |
| Beeswax | 3.33% |
| Paraffin Wax | 3.33% |
| Euphorbia Cerifera (Candelilla) Wax | 5.20% |
| Ozokerite | 3.00% |
| Copernicia Cerifera (Carnauba) Wax | 2.50% |
| Simmondsia Chinensis (Jojoba) Seed Oil | 8.00% |
| Propylparaben | 0.10% |
| Part B | |
| Polyglyceryl-4 Isostearate | 1.00% |
| Mucor Miehei Extract, Butylene Glycol, and N-Acetylglucosamine (Actipeptide ™ M, Active Organics) | 5.00% |

Mix and heat Part A to 80° C. Pre-mix Part B; add to Part A. Mix and pour into container.

Face Mask

| Part A | |
|---|---|
| Deionized Water | 59.960% |
| Aloe Barbadensis Leaf Juice (Activera ™ 10X, Active Organics) | 5.000% |
| Glycerin | 4.000% |
| Caffeine | 0.100% |
| Acacia Gum | 0.300% |
| Chromium Oxide Green | 0.500% |
| Titanium Dioxide | 3.000% |
| Methylparaben | 0.200% |
| Part B | |
| Glyceryl Stearate | 6.000% |
| Simmondsia Chinensis (Jojoba) Seed Oil | 1.500% |
| Tocopheryl Acetate | 0.100% |
| Propylparaben | 0.100% |
| Part C | |
| Bentonite | 11.000% |
| Part D | |
| Phenoxyethanol | 0.500% |
| Citric Acid 50% | 2.100% |
| Mucor Miehei Extract, Butylene Glycol, and N-Acetylglucosamine (Actipeptide ™ M, Active Organics) | 5.000% |
| Part E | |
| Essential Oil (Spearmint) | 0.070% |
| Essential Oil (Peppermint) | 0.070% |

Mix and heat Part A to 75° C. Mix and heat Part B to 75° C. Homogenize Part A, then add Part B continuing, mixing in the homogenizer for 5 minutes. Start to cool. At 60° C., add Part C; mix well. Continue cooling. At 45° C., add Parts D and E. Mix and cool to 25° C. End processing.

Moisturizing Shampoo

| Part A | |
|---|---|
| Deionized Water | 46.680% |
| Aloe Barbadensis Leaf Juice (Activera ® 10X, Active Organics) | 10.000% |
| Part B | |
| Sodium C14-16 Olefin Sulfonate | 18.000% |
| Cocamidopropyl Betaine | 18.000% |
| Glucamate DOE-120 | 1.000% |
| Part C | |
| Phenoxyethanol | 0.300% |
| Kathon CG | 0.020% |
| Sodium Chloride 25% Solution | qs |
| Butylene Glycol and Spiraea Ulmaria Extract (Actiphyte ® Queen of Meadow Concentrate, Active Organics) | 1.000% |
| Part D | |
| Mucor Miehei Extract, Butylene Glycol, and N-Acetylglucosamine (Actipeptide ™ M, Active Organics) | 5.000% |

Mix and heat Part A to 50° C. Add Part B to Part A; mix until clear. Add Parts C and D to Parts A and B. Mix and cool to 25° C. End processing.

Moisturizing Conditioner

| Part A | |
|---|---|
| Deionized Water | 64.670% |
| Aloe Barbadensis Leaf Juice (Activera ® 10X, Active Organics) | 5.000% |
| Panthenol | 0.200% |
| Part B | |
| Jojoba Oil | 2.000% |
| Behentrimonium Methosulfate, Cetearyl Alcohol | 4.000% |
| Stearamidopropyl Dimethylamine | 2.000% |
| Cetearyl Alcohol | 4.500% |
| PEG-100 Stearate | 0.880% |
| Glyceryl Stearate | 1.200% |
| Part C | |
| Water, Phenyl Trimethicone, Cyclomethicone, Polysilicone-11, Lecithin (Actiprime ™ 100, Active Organics) | 10.000% |
| Part D | |
| Mucor Miehei Extract, Butylene Glycol, and N-Acetylglucosamine (Actipeptide ™ M, Active Organics) | 5.000% |
| Phenoxyethanol | 0.500% |
| Methylisothiazolinone | 0.050% |

Mix and heat Part A to 75° C. Mix and heat Part B to 75° C. Add Part B to Part A. After mixing, add Part C and mix. Cool until 45° C., the add Part D. Mix and cool to 25° C. End processing.

Face Serum

| Part A | |
|---|---|
| Deionized Water | 80.850% |
| Keltrol RD | 0.250% |
| Butylene Glycol | 0.400% |
| Part B | |
| Water | 0.600% |
| Potassium Sorbate | 0.100% |
| Part C | |
| Water, Algae Extract, and Aloe Barbadensis Leaf Juice (Actisea ® 100, Active Organics) | 5.0% |
| Part D | |
| Aloe Barbadensis Leaf Juice (Activera ® 10x, Active Organics) | 5.000% |
| Phenoxyethanol | 0.600% |
| Neolone 950 | 0.050% |
| Mucor Miehei Extract, Butylene Glycol, and N-Acetylglucosamine (Actipeptide ™ M, Active Organics) | 5.000% |
| Part E | |
| Water | 2.000% |
| Allantoin | 0.1% |
| Disodium EDTA | 0.05% |

Mix Part A. Add pre-dissolved Part B; mix until uniform. Add Part C; mix until uniform. Add Part D; mix well. Add pre-dissolved Part E, mix until uniform. End processing.

Clinical Testing

Reduction in the appearance of signs of aging are documented using four types of clinical studies well-known to persons of skill in the art: (i) skin hydration based on impedance measurements; (ii) skin firmness based on ballistometry; (iii) wrinkle reduction via surface facial line assessment; (iv) skin smoothness via replicas and digital image analysis. In each study, twelve female subjects, ages 40-60, with normal and/or normal to dry skin, exhibiting the signs of aging, apply the following formula twice daily in an amount of 3 mg/cm$^2$:

| Part A | |
|---|---|
| Water | 70.40 |
| Butylene Glycol | 10.00 |
| Part B | |
| Stearic Acid | 2.50 |
| Caprylic/Capric Triglyceride | 3.00 |
| Glyceryl Stearate | 3.50 |
| PEG-100 Stearate | 2.00 |
| Cetearyl Alcohol | 1.00 |
| Ceteareth-20 | 1.00 |
| Dimethicone | 0.60 |
| Part C | |
| Phenoxyethanol | 0.72 |
| Methylparaben | 0.16 |
| Ethylparaben | 0.04 |
| Propylparaben | 0.02 |
| Butylparaben | 0.04 |
| Isobutylparaben | 0.02 |
| Part D | |
| Actipeptide ™ M | 5.00 |

The above formula is produced according to the following procedure: Mix and heat Part A to 75° C. Mix and heat Part B in a separate container to 75° C. Add Part B to Part A. Mix well and cool batch to 45° C. Add Part C to batch while mixing. Add Part D. Mix and cool to 25° C.

The test subjects are not currently using Retin-A, or analogs, corticosteroids, benzoyl peroxide, and/or topical antibiotics and have not used these products within the past six months. The subjects likewise have not had facial peels or dermabrasion within the last year. Additionally, the subjects do not have psoriasis, eczema, or atopic dermatitis.

One week prior to entering the study, subjects discontinue using skin care products (e.g., moisturizer, sunscreen, liquid make-up). They are also given a bar of soap (Neutrogena) with which to wash their entire facial area as often as they choose. This skin equilibration period helps to ensure that all subjects are at a baseline value and helps to minimize possible confounding from previous skin care regimens. On the first day after the one-week skin equilibration, all study participants are given instructions on how to use the test products. Subjects are instructed to cleanse only with the Neutrogena soap for the remainder of the eight-week study.

Skin moisture content is assessed via impedance measurements on the cheek area of subjects using a Novameter DPM. At the end of the one week skin equilibration period, two separate measurements are taken on each subject and averaged. The baseline average of 95.8 indicates the relatively dry skin conditions of the subjects. As summarized in the table below, significant increases in skin moisture content of 16.5%, 19% and 24.2% in skin moisture content are observed after two, four and eight weeks of treatment:

| Subject | Baseline | 2 weeks | 4 weeks | 8 weeks |
| --- | --- | --- | --- | --- |
| 1 | 90 | 112 | 111 | 113 |
| 2 | 98 | 101 | 107 | 110 |
| 3 | 98 | 116 | 121 | 124 |
| 4 | 98 | 110 | 111 | 114 |
| 5 | 95 | 114 | 116 | 119 |
| 6 | 90 | 100 | 104 | 121 |
| 7 | 93 | 122 | 124 | 122 |
| 8 | 94 | 115 | 114 | 118 |
| 9 | 97 | 121 | 127 | 131 |
| 10 | 99 | 111 | 117 | 115 |
| 11 | 95 | 112 | 110 | 115 |
| 12 | 103 | 106 | 106 | 126 |
| Average | 95.8 | 111.7 | 114.0 | 119.0 |
| % Change |  | 16.5 | 19.0 | 24.2 |

Skin firmness is assessed using a ballistometer (custom—Dermac Labs, Conn.). As is known to those of skill in the art, a ballistometer drops a pendulum on the skin surface and measures the resultant bouncing pattern. More particularly, the ratio of the height of the first and second rebound peaks are calculated. As summarized in the following table, after four and eight weeks of treatment, significant increases in skin firmness of 21.8% and 25.9% are found.

| Subject | Baseline | 2 weeks | 4 weeks | 8 weeks |
| --- | --- | --- | --- | --- |
| 1 | 3.23 | 3.11 | 2.56 | 2.42 |
| 2 | 4.12 | 3.45 | 3.05 | 3.04 |
| 3 | 4.67 | 4.64 | 3.2 | 2.87 |
| 4 | 4.05 | 3.9 | 3.34 | 3.19 |
| 5 | 5.12 | 4.67 | 4.03 | 3.77 |
| 6 | 3.8 | 3.6 | 2.96 | 2.8 |
| 7 | 4.03 | 3.54 | 3.21 | 3.04 |
| 8 | 3.5 | 3.26 | 2.93 | 2.7 |
| 9 | 3.56 | 3.4 | 2.86 | 2.67 |
| 10 | 3.78 | 3.67 | 3.05 | 3.1 |
| 11 | 4.1 | 3.86 | 3.05 | 2.89 |
| 12 | 3.92 | 3.86 | 3.2 | 2.97 |
| Average | 3.99 | 3.75 | 3.12 | 2.96 |
| % Change |  | −6.1 | −21.8 | −25.9 |

Superficial facial lines (SFLs) are assessed using the method of Packman, and Gans, "Topical Moisturizer: Quantification of their effects on Superficial Facial Lines," *J. Soc. Cosmet. Chem.* 29: 79-90, (1978). At two weeks, four weeks and eight weeks, depth, shallowness and the number of SFLs are scored within a defined area around the eye. Reductions of 22.4%, 36.4% and 42.3% are observed after two, four and eight weeks.

| Subject | Baseline | 2 weeks | 4 weeks | 8 weeks |
| --- | --- | --- | --- | --- |
| 1 | 21 | 17 | 14 | 12 |
| 2 | 14 | 11 | 10 | 9.5 |
| 3 | 16.5 | 14 | 11.5 | 11 |
| 4 | 22 | 17 | 12.5 | 12 |
| 5 | 17.5 | 13 | 9 | 10 |
| 6 | 19 | 15 | 13 | 12 |
| 7 | 16 | 12 | 11 | 10 |
| 8 | 18 | 12.5 | 10 | 8.5 |
| 9 | 19.5 | 16 | 13 | 11 |
| 10 | 22 | 18.5 | 14.5 | 12 |
| 11 | 18.5 | 12.5 | 10 | 10 |
| 12 | 17 | 13 | 12 | 9.5 |
| Average | 18.42 | 14.29 | 11.71 | 10.63 |
| % Change |  | −22.4 | −36.4 | −42.3 |

Changes in fine lines and wrinkles and skin texture are also measured by taking Silflo Replicas of the left and right canthus areas. Adhesive rings are placed on each canthus area and dental silicon replicating material is poured inside the rings. As soon as the silicon dries (2-3 minutes), it is removed, the replicas are labeled with the subject number and date. Black and white photographs of the replicas are scanned and converted into black and white pixels, where black pixels highlight lines and wrinkles. The total number of white (non-wrinkle) and black (wrinkles and lines) pixels are compared to a predetermined threshold value. Reductions in fine lines and wrinkles of 14.1%, 21%, and 30.1% are observed, respectively, at two four and eight weeks.

| Subject | Baseline | 2 weeks | 4 weeks | 8 weeks |
| --- | --- | --- | --- | --- |
| 1 | 10294 | 10203 | 9506 | 8324 |
| 2 | 13211 | 11045 | 10405 | 9045 |
| 3 | 16237 | 12495 | 11450 | 10302 |
| 4 | 16203 | 12402 | 10890 | 9940 |
| 5 | 11034 | 9820 | 9340 | 7894 |
| 6 | 12405 | 10808 | 9937 | 8094 |
| 7 | 13002 | 11056 | 10485 | 10003 |
| 8 | 9579 | 9304 | 8765 | 6794 |
| 9 | 12200 | 10365 | 10038 | 8905 |
| 10 | 8567 | 8340 | 8244 | 7892 |
| 11 | 12345 | 10869 | 9450 | 8732 |
| 12 | 15230 | 12405 | 10203 | 9122 |
| Average | 12525.58 | 10759.33 | 9892.75 | 8753.92 |
| % Change |  | −14.1 | −21.0 | −30.1 |

DNA Microarray Analysis

The effect of proteinaceous extract of R. miehei that is substantially devoid of acid-protease activity on the expression of certain genes are analyzed using DNA microarrays as described below.

Cultured cells are grown in a 6-well plate until confluent using appropriate culture conditions. Upon reaching confluency, three of the six wells are treated with culture media supplemented with test material at a concentration of 1%. The remaining three wells are treated with culture media alone and act as a control. After applying the test material, the cells are incubated for 24 hours at $37\pm2°$ C. and $5\pm1\%$ $CO_2$. At the end of the incubation period, the culture media is removed via aspiration and the cells are washed once with cold phosphate buffered saline ("PBS") using approximately 1 ml per well. After the wash, a trypsin/EDTA solution is added to the wells to detach the cells. Trypsin neutralizing solution is then added to the wells. The treated cells and the untreated cells are pooled into separate 15 ml centrifuge tubes and pelleted by centrifuging at loot RPM at $4\pm2°$ C. After removing the supernatant, the pelleted cells are lysed by adding 300 ml of guanidinium thiocyanate lysis solution to each tube and then repeatedly drawing and releasing the solution into the pipette until the cell pellet is dissolved. The cell lysates are stored at $-75°$ C. until the RNA extraction process as described below is completed.

Alternatively, cultured tissues may be used. Tissue samples are removed from the shipping tray and placed into a 6-well plate containing 2.5-5.0 ml of assay medium ($37\pm2°$ C.). They are incubated for at least 24 hours at $37\pm2°$ C. and $5\pm1\%$ $CO_2$. After this initial incubation, the assay medium is replaced with 2.5-5.0 ml of fresh medium ($37\pm2°$ C.). 25-50 ml of test material or phosphate buffered saline (negative control) are applied directly onto the surface of the tissue. The 6-well plates are then incubated at $37\pm2°$ C. and $5\pm1\%$ $CO_2$ for 24 hours. Thereafter, the tissue samples are washed at least once with 100 ml of PBS and placed into a 1.5 ml centrifuge tube containing 10-12 volumes of guanidinium thiocyanate lysis solution. The tissues are minced with fine tipped scissors and homogenized until thoroughly disrupted. After homogenization, the tissues are then centrifuged at 15,000 RPM for 10 minutes. The supernatant is transferred to a new tube. The pellet (tissue debris) is discarded. The tissue homogenate is then stored at $-75°$ C. until the RNA extraction process as described below is completed.

RNA Isolation

RNA isolation is performed using the RNAqueous Kit from Ambion Inc. (Austin, Tex.). To the cell lysates or tissue homogenates prepared above, an equal volume of 64% ethanol is added and the tubes are vortexed. Up to 700 ml of the mixture is transferred to a glass fiber filter cartridge, which is loaded into a 1.5 ml collection tube and the cartridge is centrifuged for 1 minute at 14,000 RPM. The flow through is discarded. Any remaining mixture is loaded into the filter cartridge and the centrifugation process is repeated until all of the mixture has been processed. The filter is then washed to remove any residual cellular debris from the RNA bound to the glass fibers by applying 700 ml of a first wash solution (1 time) and 500 ml of a second wash solution (2 times) to the filter cartridge and centrifuging at 14,000 RPM for 1 minute to pass each wash through the cartridge. The flow through is discarded after each wash. After the final wash, one final spin is performed without wash solution to remove any residual wash solution in the filter cartridge. The RNA bound to the glass fibers within the cartridge is then be eluted by applying 30 ml of Tris-EDTA buffer (10 mM Tris-HCl, 1 mM EDTA, preheated to 70-80° C., hereinbelow "TE buffer") to the cartridge and centrifuging the cartridge in a new collection tube at 14,000 RPM for one minute. For samples prepared from cell lysates and small tissues, the elution process is repeated with an additional 30 ml of preheated TE buffer. For samples prepared from larger tissues (i.e., full thickness tissues) the elution process is repeated two additional times. After the RNA is eluted, RNA concentration is quantified using a Ribogreen assay. RNA quality is assessed via gel electrophoresis.

RNA Concentration Assay

Ribogreen reagent is provided as a stock solution in DMSO. Prior to use, the reagent is diluted 2000 fold in TE buffer. The RNA assay requires 200 ml of diluted Ribogreen reagent per sample to be tested and 1 ml of the reagent for the standards. Once prepared, the diluted reagent is stored protected from light. A series of RNA standards are prepared by diluting purified ribosomal RNA derived from E. coli to the following concentrations: 2 mg/ml, 1 mg/ml, 200 ng/ml, 40 ng/ml and 0 ng/ml (blank). Prior to assaying, the RNA samples prepared above are diluted 1000 fold in TE buffer. For the RNA assay, 100 ml of the diluted samples or standards are transferred to the wells of a black 96-well plate. The samples and standards are assayed in duplicate. After the samples/standards are added to the plate 100 ml of diluted Ribogreen assay reagent is added to the wells and the plate is gently mixed and allowed to incubate for 5-10 minutes protected from the light. After this incubation, the plate is read with a fluorometer using an excitation wavelength of 500 nm and an emission wavelength of 525 nm.

RNA Gel Electrophoresis

A 1% RNA gel is prepared by adding 0.3 g agarose to 21.6 ml diethylpyrocarbonate (DEPC) treated water. The agarose is dissolved by boiling the water in a microwave oven. After the solution is cooled to approximately 55° C., 5.4 ml of formaldehyde and 3.0 ml 10×MOPS (0.2 M MOPS [pH 7.0], 20 mM sodium acetate, 10 mM EDTA, made in DEPC $H_2O$ and filter sterilized). After mixing, the agarose gel is cast in the horizontal gel apparatus with loading slots placed on the side of the gel closest to the negative terminal. The gel is allowed to set for at least 1 hour at room temperature. While the gel is setting, 175 ml of 1×MOPS is prepared by diluting the 10× stock. After the gel is set, the comb is removed and the buffer chamber of the gel apparatus is filled with 150-175 ml 1×MOPS (enough buffer is added to cover the gel with approximately 3 mm of buffer). The cover is placed on the apparatus, the electrical leads are attached to the power source, and the empty gel is run at 40 V (4 V/cm) for 5-10 minutes. While the gel is running, the RNA samples are prepared by transferring approximately 1 mg of each sample RNA to a 600 ml PCR tube. DEPC $H_2O$ is used to bring the total volume of all the samples to a common level and then 1-3 volumes of a gel-loading buffer (i.e. 5% glycerol, 1 mM EDTA, 0.025% bromophenol blue, 0.025% xylene cyanol FF, 20% formaldehyde, 50% formamide, 10 mg/ml ethidium bromide) are added. The samples are denatured by placing them at 65-70° C. for 5-15 minutes and then placed on ice to cool. The samples are then carefully loaded into the lanes (each loading slot can hold 10-15 ml of sample, depending upon the thickness of the gel) and run on the gel at 40 V for 1-3 hours. At the end of the run, the RNA is visualized by placing the gel on a UV transilluminator. An RNA sample is used for subsequent processing if both the 18S and 28S ribosomal bands are clearly visible and there is little or no staining below the 18S band.

mRNA Amplification mRNA is amplified using the MessageAmp aRNA kit from Ambion Inc.

First Strand cDNA Synthesis: To start the first strand synthesis, 5 mg of total RNA for each sample are added to 600 ml PCR tubes and the total volume of liquid in the tube is adjusted to 12 ml with DEPC $H_2O$. To each tube, 1 ml of T7

Oligo(dT) primer is added and the tube is incubated at 70±2° C. for 10 minutes to denature the RNA and is then placed on ice to allow the primer to anneal to the poly A ends of the mRNA. After cooling, 2 ml of 10× first strand buffer, 1 ml of RNAse inhibitor and 4 ml of dNTP mix is added to each tube, and the tube is placed at 42° C. As soon as the tube is heated, 1 ml of reverse transcriptase is added and the tubes are returned to 42±2° C. for 2 hours. At the end of the two hours, the tubes are briefly centrifuged to collect all of the fluid at the bottom of the tube and then placed on ice.

Second Strand Synthesis and cDNA Purification: For the synthesis of the second strand of cDNA the following ingredients are added sequentially to the tubes: 63 ml DEPC $H_2O$, 10 ml 10× second strand buffer, 4 ml dNTP mix, 2 ml DNA Polymerase and 1 ml of RNAse H. The tube is mixed and then incubated at 16±2° C. for 2 hours. Towards the end of the 2 hour incubation, a sufficient quantity of DEPC $H_2O$ is warmed to 50±2° C., and a cDNA purification filter cartridge is equilibrated with 50 ml of cDNA binding buffer (one cartridge per sample) for at least 5 minutes. After the samples are finished incubating, 250 ml of cDNA binding buffer are added to each tube and thoroughly mixed. The contents of the PCR tube are then transferred to the cDNA purification filter cartridge. The cartridge is then placed in a collection tube and centrifuged at 10,000 RPM for 1 minute. The flow-through is discarded and 650 ml of cDNA wash solution is added to the cartridge. The cartridge is centrifuged again, the flow-through is discarded, and is then centrifuged one additional time to ensure that the wash buffer has been completely emptied from the filter. The cDNA is eluted by applying 10 ml of preheated DEPC $H_2O$ to the filter and centrifuging the filter in a new collection tube at 10,000 RPM for one minute. This elution is performed one additional time to give a total volume of 16-18 ml of cDNA solution.

In Vitro Transcription to Synthesize aRNA and aRNA Purification

The in vitro transcription begins by adding the following to the cDNA solution: 4 ml each of T7 ATP solution, T7 CTP solution, T7 GTP solution, T7 UTP solution, 4 ml of 10× Reaction buffer, and 4 ml of T7 enzyme mix. The tube is mixed and then incubated at 37±2° C. for 6-14 hours. Towards the end of the incubation, a sufficient volume of Elution Solution is warmed to 50-60° C. and an aRNA filter cartridge is equilibrated with 100 ml of aRNA binding buffer for at least 5 minutes. At the end of the incubation period, 350 ml of aRNA binding buffer is added to the sample tubes and thoroughly mixed. An additional 250 ml of absolute ethanol is also added to each tube. The mixture is then transferred to an aRNA filter cartridge; the cartridge is then inserted into a collection tube and centrifuged at 10,000 RPM for 1 minute. The flow-through is discarded and 650 ml of aRNA wash buffer is added to the cartridge followed by centrifuging at 10,000 RPM for one minute. After discarding the flow through, the cartridge is spun one final time to remove all traces of the wash buffer. The cartridge is then transferred to a new collection tube. 25 ml of pre-warmed Elution Solution is added to the cartridge. The cartridge is incubated for 2 minutes at room temperature and then aRNA is eluted by centrifuging for 1 minute at 10,000 RPM. This elution is performed one additional time to give a total volume of 45-50 ml of aRNA solution. The final concentration of the aRNA is determined by the Ribogreen assay described above. In addition, the quality of the aRNA is checked via gel electrophoresis as described above. An aRNA sample is used for subsequent processing if a broad band of RNA is observed.

Labeling and Purification of aRNA aRNA is labeled with fluorescent dyes using the PerkinElmer ASAP RNA Labeling Kit. Two tubes are prepared for the labeling process—for the untreated sample Cy3 labeling (green), and for the treated sample Cy5 labeling (red). To the Cy3 tube add 2 mg of aRNA prepared from the untreated/control sample and add enough DEPC $H_2O$ to bring the total volume up to 4 ml. To the Cy5 tube add 2 mg of aRNA prepared from the sample treated with the test material and add enough DEPC $H_2O$ to bring the total volume up to 4 ml. To both tubes, add 5 ml of ASAP labeling buffer and 1 ml of the specific dye for the tube (Cy3 or Cy5). Incubate the tubes for 15 minutes at 85±2° C. At the end of the 15 minutes, place the tubes on ice to cool and then add 2.5 ml of ASAP stop solution to each tube. The above proportions are sufficient for analyzing one microarray chip. If more chips are to be used then the labeling is increased proportionately.

To purify the labeled aRNA, a microcon YM-30 filter column is inserted into a collection tube and filled with 400 ml of TE buffer. The Cy3 and Cy5 probes are combined (12.5 ml of each) and then added to the microcon filter and thoroughly mixed with the TE buffer. The filter is centrifuged at 12,000 RPM for 8 minutes and the flow through is discarded. The column is washed twice with 400 ml of TE buffer, discarding the flow though each time. After the final wash, the filter column is inverted, placed into a new collection tube and centrifuged at 12,000 RPM for 2 minutes to collect the probe (the probe is concentrated in a volume of 2-30 ml of residual TE buffer).

Microarray Hybridization and Washing

For hybridization, 45 ml of 10× control target RNA (supplied with Agilent Technologies In Situ Hybridization Kit) is mixed with 160 ml of DEPC water and 9 ml of 25× Agilent Fragmentation Buffer. This mixture is incubated at 60° C. for approximately 30 minutes in a hybridization oven. At the end of the incubation, 225 ml of Agilent Hybridization Buffer is added along with the fluorescent aRNA probes prepared above. The mixture is then incubated at 70° C. for 5-10 minutes in a waterbath. During this incubation period, an Agilent SUREHYB hybridization chamber is prepared by inserting a glass gasket slide into the bottom half of the chamber. At then end of the incubation, the hybridization mixture (approximately 450 ml) is applied to the glass gasket slide and an Agilent Human 1A Oligo Microarray Chip is placed face down on top of the gasket such that the hybridization solution is sandwiched between the glass gasket slide and the microarray face of the chip. The top half of the chamber is attached and the connecting thumbscrew tightened. After verifying that there is good bubble formation in the chamber, it is placed into the hybridization oven for approximately 17 hours (60° C. and rotating at 4 RPM). At then end of the hybridization period, the microarray/glass gasket is removed from the SUREHYB chamber and placed in 50 ml of a first wash solution (room temperature, 6×SSC, 0.005% Triton X-102). After the gasket has fallen away from the microarray, the array is transferred to 300 ml of fresh wash solution 1 on a magnetic stir plate. The array is washed while the solution is mixed at medium speed for 10 minutes and is then transferred to 300 ml of wash solution 2 (0.1×SSX, 0.005% Triton X-102, 4° C.) for 5 minutes. After the final wash, the array is centrifuged at 500 RPM for 5 minutes until dry.

Microarray Scanning and Analysis

The microarrays are scanned with an Axon GenePix 4100A Scanner with the scanning resolution set to 10 mm and analyzed with GenePix Pro software. During the initial scan the PMT gains for the scanner are adjusted such that the Cy5/Cy3 image count ratios are between 0.88 and 1.12.

To derive the standard curve for the Ribogreen assay, the relative fluorescent units versus the known RNA concentrations in mg/ml for the standards is plotted and subjected to regression analysis to establish the line that best fits these data points. Mean RFU values for the test materials and untreated samples are then used to estimate the amount of RNA present in each sample.

The level of gene expression is related to the fluorescence intensity of the probed gene marker on the microarray. Fluorescence measurements between the Cy3 and Cy5 probes are normalized. The total fluorescent signal for both dyes is normalized with a correction factor such that the ratio of total intensities for both dyes equal to one.

Criteria for evaluating changes in gene expression are known to those of ordinary skill in the art and include the following: First, the ratio of Cy3/Cy5 (untreated/treated) fluorescence intensity is greater than 1.5 or less than 0.66. (This relates to a change in gene expression of at least +/−30%.) Second, the fluorescence intensity of the gene marker is greater than the background intensity. Third, the gene feature is clearly marked specifically by the aRNA probes and is not due to non-specific fluorescence. The first two criteria are filtered via computer analysis. The last criterion requires visual inspection of the array.

Ratios of greater than about 1.3 are interpreted to indicate that a gene is upregulated by the treatment, whereas ratios of less than about 0.7 are interpreted to indicate a downregulated gene. Thus, a ratio of 1.3, where the treated value is 130% of the untreated value, indicates a 30% increase in gene expression. Similarly, a ratio of 0.7 means that the treated value was 70% of the untreated value, indicating a 30% decrease in gene expression.

The following results are observed after completing the micro-array analysis as described above:

| | |
|---|---|
| Type 1 collagen, alpha 1 subunit | 1.31 |
| MMP1 | 0.495 |
| Fibronectin | 1.64 |
| Vimentin | 1.346 |
| Procollagen-lysine 2-oxoglutarate 5-dioxygenase | 2.10 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A dermatocosmetic composition for increasing levels of collagen in the skin comprising:
 a therapeutically-effective amount of a proteinaceous extract of *Rhizomucor miehei* substantially devoid of acid-protease activity, wherein the overall acid protease specific activity within the composition is less than about 500 HUT units/mg;
 one or more surfactants; and
 a dermatologically-acceptable carrier.

2. The composition of claim 1, wherein the overall acid protease specific activity is less than about 50 HUT units/mg.

3. The composition of claim 1, wherein the overall acid protease specific activity is less than about 10 HUT units/mg.

4. The composition of claim 1, wherein the dermatologically-acceptable carrier is an emulsion.

5. A composition for stimulating collagen synthesis comprising:
 a therapeutically-effective amount of a proteinaceous extract of *Rhizomucor miehei* substantially devoid of acid-protease activity, wherein the overall acid protease specific activity within the composition is less than about 500 HUT units/mg;
 one or more surfactants; and
 a dermatologically-acceptable carrier.

6. The composition of claim 5, wherein the overall acid protease specific activity is less than about 50 HUT units/mg.

7. The composition of claim 5, wherein the overall acid protease specific activity is less than about 10 HUT units/mg.

8. The composition of claim 5, wherein the dermatologically-acceptable carrier is an emulsion.

9. A composition for modulating the expression of one or more genes that code for collagen synthesis comprising:
 a therapeutically-effective amount of a proteinaceous extract of *Rhizomucor miehei* substantially devoid of acid-protease activity, wherein the overall acid protease specific activity within the composition is less than about 500 HUT units/mg;
 one or more surfactants; and
 a dermatologically-acceptable carrier.

10. The composition of claim 9, wherein the overall acid protease specific activity is less than about 50 HUT units/mg.

11. The composition of claim 9, wherein the overall acid protease specific activity is less than about 10 HUT units/mg.

12. The composition of claim 9, wherein the expression is increased or decreased.

* * * * *